US012604920B2

(12) United States Patent　　(10) Patent No.:　US 12,604,920 B2
Mizobuchi　　(45) Date of Patent:　Apr. 21, 2026

(54) ENZYME COMPOSITION FOR FOOD PRODUCTS

(71) Applicant: Nagase Viita Co., Ltd., Okayama (JP)

(72) Inventor: Hisanori Mizobuchi, Kyoto (JP)

(73) Assignee: Nagase Viita Co., Ltd., Okayama (JP)

( * ) Notice: Subject to any disclaimer, the term of this patent is extended or adjusted under 35 U.S.C. 154(b) by 265 days.

(21) Appl. No.: 18/553,119

(22) PCT Filed: Mar. 30, 2022

(86) PCT No.: PCT/JP2022/016266

§ 371 (c)(1),
(2) Date: Sep. 28, 2023

(87) PCT Pub. No.: WO2022/210963

PCT Pub. Date: Oct. 6, 2022

(65) Prior Publication Data

US 2024/0188615 A1　　Jun. 13, 2024

(30) Foreign Application Priority Data

Mar. 31, 2021　(JP) .................................. 2021-060154

(51) Int. Cl.
| A23L 29/00 | (2016.01) |
| A23C 9/12 | (2006.01) |
| A23C 11/10 | (2021.01) |
| A23C 13/12 | (2006.01) |
| A23L 11/30 | (2016.01) |

(Continued)

(52) U.S. Cl.
CPC ............ *A23L 29/06* (2016.08); *A23C 9/1216* (2013.01); *A23C 11/103* (2013.01); *A23C 13/12* (2013.01); *A23L 11/33* (2016.08); *A23L 13/30* (2016.08); *A23L 13/48* (2016.08); *A23L 15/25* (2016.08); *A23L 17/65* (2016.08); *A23L 31/15* (2016.08); *C12N 9/485* (2013.01)

(58) Field of Classification Search
CPC .......... A23L 29/06; A23L 15/25; A23L 17/65; A23L 11/33; A23L 13/48; A23L 13/30; A23L 31/15; A23C 9/1216; A23C 11/103; A23C 13/12; C12N 9/485
USPC ........................................................ 426/42
See application file for complete search history.

(56) References Cited

U.S. PATENT DOCUMENTS

| 6,800,467 B1 | 10/2004 | Blinkovsky et al. |
| 2006/0068056 A1 | 3/2006 | Sakamoto et al. |

FOREIGN PATENT DOCUMENTS

| CN | 111202234 | 5/2020 |
| JP | 2-222641 | 9/1990 |

(Continued)

OTHER PUBLICATIONS

Arima et al., Study on peptide hydrolysis by aminopeptidases from Streptomyces griseus, Streptomyces septatus and Aeromonas proteolytica, Appl Microbiol Biotechnol (2006) 70: 541-547, Published Aug. 4, 2005. (Year: 2005).*

(Continued)

*Primary Examiner* — Brent T O'Hern
(74) *Attorney, Agent, or Firm* — HSML P.C.

(57) ABSTRACT

Provided is an enzyme composition that can be used to produce food products with less contaminants and excellent flavor and texture. An enzyme composition for food products containing a peptidase and having substantially no contaminating activity.

7 Claims, 2 Drawing Sheets

Specification includes a Sequence Listing.

(51) Int. Cl.

| | | |
|---|---|---|
| *A23L 13/30* | (2016.01) | |
| *A23L 13/40* | (2023.01) | |
| *A23L 15/00* | (2016.01) | |
| *A23L 17/00* | (2016.01) | |
| *A23L 31/15* | (2016.01) | |
| *C12N 9/48* | (2006.01) | |

(56) References Cited

FOREIGN PATENT DOCUMENTS

| | | | | |
|---|---|---|---|---|
| JP | 2005-052052 | | | 3/2005 |
| JP | 2005-218319 | | | 8/2005 |
| JP | 2007-319063 | | | 12/2007 |
| JP | 2007319063 | A | * | 12/2007 |
| WO | 2018/192830 | | | 10/2018 |
| WO | 2004/105503 | | | 12/2024 |

OTHER PUBLICATIONS

Arima, et al., "Study on peptide hydrolysis by aminopeptidases from Streptomyces griseus, Steptomyces septatus and Aeromonas proteolytia", Appl Microbiol Biotechnol (2006) 70: 541-547.
Arima, Jiro, "Production methods of different dipeptides using aminopeptidase", [online] 2012, (http://www.cjrd.tottori-u.ac.jp/seeds_cgi/files/20120508171845_pdffile02.pdf) Please see the English Translation of the Written Opinion for a concise explanation.
Written Opinion issued in International Application No. PCT/JP2022/016266, Jun. 14, 2022, 6 pages.

* cited by examiner

ENZYME COMPOSITION FOR FOOD PRODUCTS

TECHNICAL FIELD

The present invention relates to an enzyme composition for food products.

BACKGROUND ART

Proteases are enzymes that cleave peptide bonds present in proteins and polypeptides by hydrolysis, and are used for the production of meat-derived extracts, meat tenderization, the production of amino acids, and the like. The proteases are further classified, depending on their activity, into proteinases that cleave polypeptide chains internally, aminopeptidases that cleave polypeptide chains sequentially from their amino termini, and carboxypeptidases that cleave polypeptide chains sequentially from their carboxy termini. Patent Literature 1 discloses a type of aminopeptidase.

Patent Literature 2 discloses that when an egg yolk is treated with a protease, the use of an alkaline protease having no amylase activity can suppress a change over time in the treated egg yolk.

CITATION LIST

Patent Literature

Patent Literature 1: JP 2005-218319 A
Patent Literature 2: JP 2005-52052 A

SUMMARY OF INVENTION

Technical Problem

Conventional enzyme compositions containing a protease contain contaminants such as amylase, and the flavor and texture of food products after enzymatic treatment have not been sufficient. An object of the present invention is to provide an enzyme composition that can be used to produce food products with less contaminants and excellent flavor and texture.

Solution to Problem

The present inventors have focused on contaminants contained in an enzyme composition, and have completed the present invention. The present invention relates to an enzyme composition for food products containing a peptidase and having substantially no contaminating activity.

The contaminating activity is preferably amylase activity or protease activity.

The enzyme composition for food products preferably has a A/P ratio of 0.1 or less, wherein A represents amylase activity and P represents peptidase activity.

The enzyme composition for food products preferably has a E/P ratio of 0.3 or less, wherein E represents protease activity and P represents peptidase activity.

The peptidase is preferably aminopeptidase.

The peptidase is preferably derived from a bacterium.

The bacterium is preferably an *Streptomyces*.

The enzyme composition for food products is preferably for use in the production of processed meat food products, processed seafood food products, processed egg food products, processed dairy food products, processed plant food products, insect food products, or seasonings.

The present invention also relates to a method of producing a food product, comprising a step of processing a food material with the enzyme composition for food products described above.

The food material is preferably a meat, a seafood, an egg, a milk, a plant, an insect, or a microorganism culture.

The present invention also relates to a food product containing the enzyme composition for food products described above.

The food product is preferably selected from the group consisting of a meat extract, a seafood extract, a custard sauce, a custard cream, a processed milk, a soybean food product, an insect food product, and a seasoning.

Advantageous Effect of Invention

The enzyme composition for food products of the present invention has substantially no contaminating activity, and can be therefore utilized for the production of food products with excellent flavor and texture.

DESCRIPTION OF EMBODIMENTS

<<Enzyme Composition for Food Products>>

Figure 1:
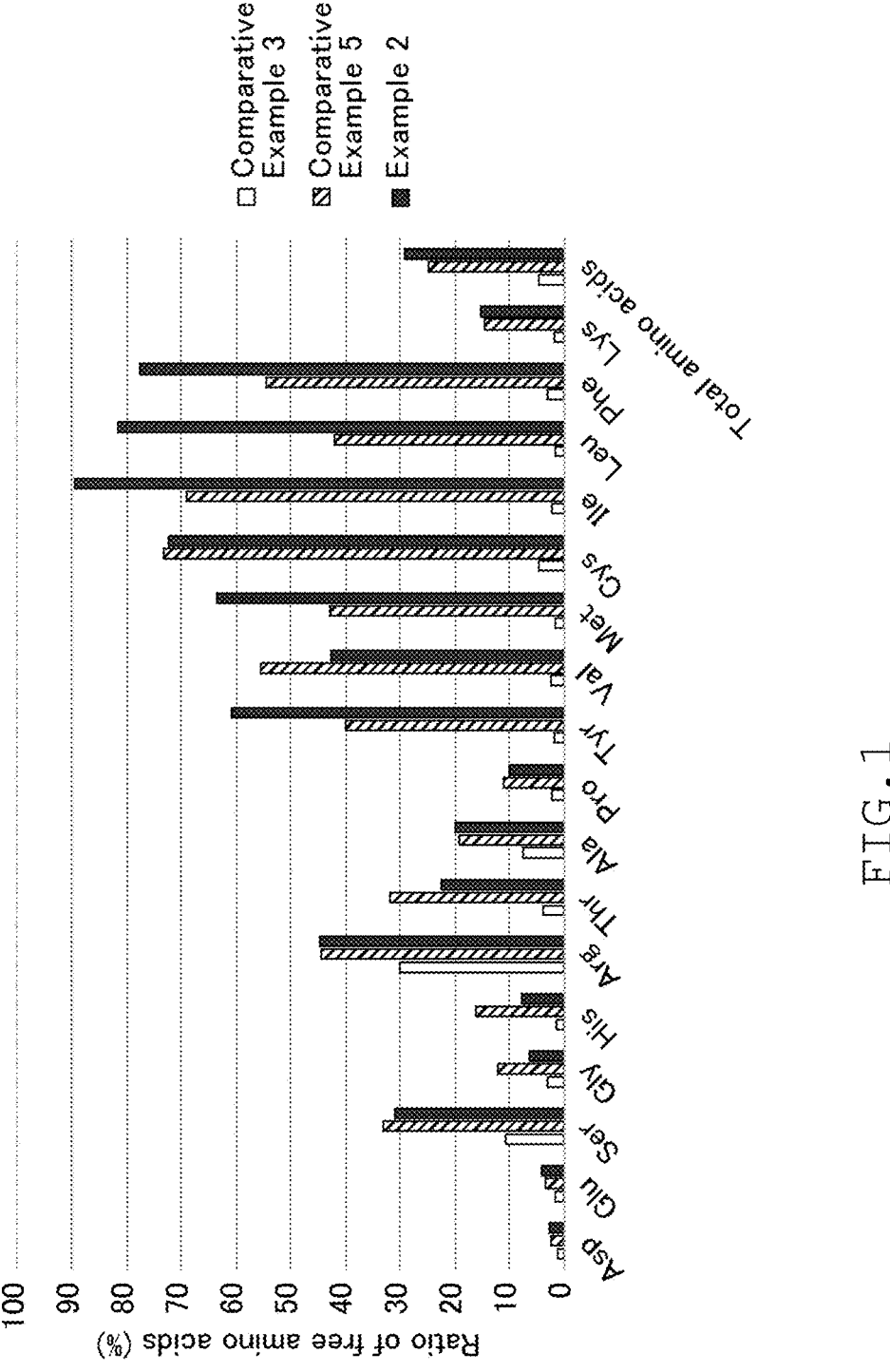
FIG. 1 shows the amount of free amino acids after enzymatic treatment of beef extract.

The enzyme composition for food products of the present invention comprises a peptidase and is characterized by having substantially no contaminating activity.

<Peptidase>

The peptidase is an enzyme that hydrolytically cleavages peptide bonds of a polypeptide chain constituting a protein, sequentially from the terminus. Examples of the peptidase include aminopeptidase that hydrolytically cleaves peptide bonds sequentially from the amino terminus, carboxypeptidase that hydrolytically cleaves peptide bonds sequentially from the carboxy terminus, dipeptidase, dipeptidyl peptidase that hydrolytically cleaves peptide bonds to produce dimers of amino acids from a polypeptide chain, and tripeptidyl peptidase that hydrolytically cleaves peptide bonds to produce trimers of amino acids from a polypeptide chain. In particular, the peptidase is preferably aminopeptidase and carboxypeptidase, more preferably aminopeptidase.

The peptidase is derived from any origin, for example, a microorganism, an animal or a plant, but the peptidase is preferably derived from a microorganism from the viewpoint of easy availability. The microorganism includes a bacterium and a fungus, and is preferably a bacterium. The bacterium and fungus include an *Streptomyces* and *Aspergillus oryzae* (koji mold).

Examples of the *Streptomyces* include microorganisms belonging to the genus *Streptomyces*, the genus *Corynebacterium*, the genus *Mycobacterium*, the genus *Rhodococcus*, and the genus *Micrococcus*. Examples of the microorganism belonging to the genus *Streptomyces* include *Streptomyces septatus, Streptomyces coelicolor*, and *Streptomyces cinnamoneus*. In particular, the peptidase is more preferably derived from the genus *Streptomyces*, even more preferably *Streptomyces septatus*, and it is particularly preferably aminopeptidase derived from *Streptomyces septatus*.

The peptidase is preferably a polypeptide of (A), (B) or (C) below:

(A) a polypeptide containing the amino acid sequence shown in SEQ ID NO: 1;

(B) a polypeptide, having a sequence identity of 85% or more with the amino acid sequence shown in SEQ ID NO: 1, which has the activity of hydrolytically cleaving the peptide bonds of a polypeptide chain sequentially from the terminus; and (C) a polypeptide, composed of an amino acid sequence having one or more amino acids deleted, inserted, substituted and/or added in the amino acid sequence shown in SEQ ID NO: 1, which has the activity of hydrolytically cleaving the peptide bonds of a polypeptide chain sequentially from the terminus.

The sequence identity between the amino acid sequence of the peptidase and the amino acid sequence shown in SEQ ID NO: 1 is preferably 85% or more, more preferably 90% or more, even more preferably 95% or more, further more preferably 98% or more, particularly preferably 99% or more. The sequence identity of the amino acid sequences is represented by (the number of positions where amino acids match between the amino acid sequence shown in SEQ ID NO: 1 and the amino acid sequence to be evaluated when comparing both amino acid sequences)÷(the total number of amino acids)×100.

The number of amino acids to be deleted, inserted, substituted and/or added is preferably 51 or less, more preferably 34 or less, even more preferably 17 or less, further more preferably 6 or less, particularly preferably 3 or less.

The peptidase is preferably the polypeptide encoded by the DNA of (a), (b), or (c) below:

(a) a DNA containing the base sequence shown in SEQ ID NO: 2;

(b) a DNA, having a sequence identity of 85% or more with the base sequence shown in SEQ ID NO: 2, which encodes a polypeptide having the activity of hydrolytically cleaving the peptide bonds of the protein sequentially from the terminus; and (c) a DNA, composed of a base sequence having one or more bases deleted, inserted, substituted and/or added in the base sequence shown in SEQ ID NO: 2, which encodes a polypeptide having the activity of hydrolytically cleaving the peptide bonds of a protein sequentially from the terminus.

The sequence identity between the base sequence of the DNA encoding the peptidase and the base sequence shown in SEQ ID NO: 2 is preferably 85% or more, more preferably 90% or more, even more preferably 95% or more, further more preferably 98% or more, particularly preferably 99% or more. The sequence identity of the base sequences is represented by (the number of positions where bases match between the base sequence shown in SEQ ID NO: 2 and the base sequence to be evaluated when comparing both base sequences)÷(the total number of bases compared)×100.

The DNA, composed of a base sequence having one or more bases deleted, inserted, substituted and/or added in the base sequence shown in SEQ ID NO: 2, which encodes a polypeptide having the activity of hydrolytically cleaving the peptide bonds of a protein sequentially from the terminus can be prepared according to any known genetic modification method.

The number of base to be deleted, inserted, substituted and/or added is preferably 155 or less, more preferably 103 or less, even more preferably 51 or less, further more preferably 20 or less, particularly preferably 10 or less.

The amino acid sequence shown in SEQ ID NO: 1 and the base sequence shown in SEQ ID NO: 2 are the amino acid sequence of the aminopeptidase of *Streptomyces* sp. strain TH-2 (accession number FERM P-173295) and the base sequence of its gene, respectively.

The peptidase to be used may be either a peptidase obtained by purifying a plant, an animal or a microorganism from which it is derived, or a peptidase obtained by a large-scale production using gene recombination technology followed by purification. A wild-type peptidase may be used, or a mutant peptidase may be used.

When the peptidase accumulates in cells of the organism from which the peptidase is derived, a method for obtaining a peptidase include a method including crushing tissues and cells followed by centrifugation or the like to provide a cell-free extract. If desired, the peptidase to be used may be a peptidase obtained by subjecting, the cell-free extract as a starting material, to purification by appropriately combining general protein purification methods such as salting-out, ion exchange chromatography, gel filtration chromatography, hydrophobic chromatography and affinity chromatography. When a peptidase is produced by extracellular secretion by a microorganism, it can be purified from the medium.

The content of the peptidase in the enzyme composition for food products is not limited, but it preferably has an activity of 100 U or more per g of the enzyme composition for food products, more preferably 500 U or more, even more preferably 1000 U or more. The higher upper limit of the peptidase content in the enzyme composition for food products is better. The upper limit is not limited, but is generally 5000 U or less per g of the enzyme composition for food products. Here, for the activity of the peptidase, the enzyme activity that generates 1 µmol of paranitroaniline per minute as measured using L-leucyl-p-nitroanilide hydrochloride as a substrate at 37° C. and pH 8.0 for 10 minutes is defined as 1 U.

<Contaminating Activity>

The enzyme composition for food products of the present invention has substantially no contaminating activity. As used herein, the term "contaminating activity" refers to an enzyme activity other than peptidase activity. The examples of the contaminating activity include amylase activity, protease activity and lipase activity. In particular, the enzyme composition for food products preferably has no amylase activity, more preferably neither amylase activity nor protease activity. As used herein, the expression "have substantially no contaminating activity" means that when a food product is produced with this enzyme composition, the food product with excellent flavor and texture can be produced.

For the contaminating amylase activity, the enzyme composition for food products preferably has a A/P ratio of 0.1 or less, wherein A [U] represents amylase activity and P [U] represents peptidase activity, more preferably 0.01 or less, even more preferably 0.001 or less. Here, for the amylase activity, the enzyme activity that reduces, the absorbance at a wavelength of 660 nm as measured using potato starch as a substrate at 40° C. and pH 6.0 for 10 minutes, by 1% per minute relative to the absorbance as measured using purified water as a control is defined as 1 U.

For the contaminating protease activity, the enzyme composition for food products preferably has a E/P ratio of 0.3 or less, wherein E (U) represents protease activity and P (U) represents peptidase activity, more preferably 0.1 or less, even more preferably 0.05 or less, further more preferably 0.02 or less. Here, for the protease activity, the amount of enzyme that causes an increase in the colored substance in a Folin's test solution equivalent to 1 µg of L-tyrosine per minute, as measured using milk casein as a substrate at 30° C. and pH 7.5 for 10 minutes is defined as 1 U.

<Optional Components>

The enzyme composition for food products may contain, in addition to the peptidase, other components that may usually be contained in enzyme compositions, to the extent that the effects of the present invention are not inhibited. Examples of such components include an excipient, a pH adjuster, a preservative, a thickening polysaccharide, an emulsifier, an inorganic salt, an amino acid and an enzyme. The content of these components is any amount, can be selected by those skilled in the art.

Examples of the excipient include dextrin, trehalose, grain flour such as rice flour or wheat flour.

Examples of the pH adjuster include an organic acid such as ascorbic acid, acetic acid, dehydroacetic acid, lactic acid, citric acid, gluconic acid, succinic acid, tartaric acid, fumaric acid, malic acid or adipic acid, and a sodium (Na) salt, a calcium salt (Ca) and a potassium (K) salt of such an organic acid; and an inorganic acid such as carbonic acid, phosphoric acid or pyrophosphate, and a Na salt and a K salt of such an inorganic acid.

Examples of the preservative include propionic acid, a salt of propionic acid, a salt of sulfurous acid, a salt of benzoic acid, sorbic acid and a salt of sorbic acid. Examples of the salt include a sodium (Na) salt, a calcium (Ca) salt and a potassium (K) salt and a polyamine salt.

Examples of the thickening polysaccharide include a modified starch, a gum, alginic acid, an alginic acid derivative, pectin, carrageenan, curdlan, pullulan, gelatin, a cellulose derivative, agar, tamarind, *psyllium* and glucomannan.

Examples of the emulsifier include a glycerin fatty acid ester, a polyglycerin fatty acid ester, a sucrose fatty acid ester, a propylene glycol fatty acid ester, a sorbitan fatty acid ester, lecithin, enzymatically degraded lecithin and saponin.

Examples of the inorganic salt include sodium chloride, ammonium sulfate, sodium sulfate, calcium chloride, and a polymeric phosphate.

Examples of the amino acid include aspartic acid, threonine, serine, asparagine, glutamic acid, glutamine, proline, glycine, alanine, valine, cystine, methionine, isoleucine, leucine, tyrosine, phenylalanine, histidine, lysine, tryptophan and arginine.

The method of producing the enzyme composition for food products is not limited as long as the enzyme composition for food products contains peptidase and has substantially no contaminating activity. Examples of the method include a method including mixing peptidase and an excipient with a mixer. Examples of the mixer include rotary-type, stationary and hybrid mixers. The mixer can be appropriately selected depending on the activity value and amount of interest and the type of excipient.

The form of the enzyme composition for food products is not limited, and examples thereof include a powder form, a granule form, a liquid form, a paste form and a solid form. When the enzyme composition for food products is in a powder form, it may be a composition prepared by dissolving the peptidase in a solvent such as water followed by optionally blending an excipient such as dextrin into the solution and drying it to form a powder.

<<Food Product and Production Method Thereof>>

The method of producing a food product of the present invention is characterized by including a step of processing a food material with the enzyme composition for food products described above.

In the step of processing a food material, the food material is contacted with the enzyme composition for food products to allows the peptidase to act on a protein contained in the food material. The food material is not limited as long as it contains a protein. Examples of the food material include a meat, a seafood, an egg, a milk, a plant, an insect, or a microorganism culture and a cultured meat. Examples of the meat include a beef, a chicken, a pork, a mutton or lamb, a boar meat, a bear meat and a venison, and extracts of such a meat can be also applied. Examples of the seafood include mackerel, sardine, tuna, salmon, bonito, squid, octopus, a crustacean, a seaweed, and a shellfish such as oyster, scallop, short-necked clam, freshwater clam or clam. Examples of the egg include a chicken egg and a quail egg, and both the yolk and white of such an egg can be applied. Examples of the milk include a cow milk, a goat milk, a camel milk, a donkey milk, a horse milk and a sheep milk. Examples of the plant include soybean, pea, wheat and brown rice. Examples of the insect include cricket and mealworm. Examples of the microorganism include a yeast, a *Lactobacillus* and *Aspergillus oryzae* (koji mold), and examples of the microorganism culture include cultured cell mass and culture solution from the microorganism.

The conditions during allowing the peptidase to act on the food material are not limited. However, the temperature is preferably 0° ° C. to 75° C., more preferably 35° C. to 75° C., even more preferably 40° ° C. to 65° C. The treatment time is preferably 0.5 to 3 hours. After allowing the peptidase to act on the food material, the food material may be heated. When heated to 80° C. or more, the peptidase is inactivated, and digested and absorbed in the body in the same manner as other proteins contained in food material.

Examples of the food product to be produced by the production method of the present invention include a processed food product containing any of a meat, a seafood, an egg, a milk, a plant, an insect and a microorganism culture alone or in combination of two or more thereof. Examples of the processed meat food product include a sausage and a ham. Examples of the processed seafood food product include a chikuwa and a kamaboko. Examples of the processed dairy food product include a processed milk, a cheese, and a yogurt. Examples of the processed plant food product include a soybean food product. Examples of the insect food product include a cookie and a rice cracker. Examples of the processed food product containing a microorganism culture include seasonings such as a yeast extract, a soy sauce and a mirin. Examples of the processed food product containing a combination of two or more food materials include a custard sauce, a custard cream and a potato salad.

The use of the enzyme composition for food products enables the peptide bonds of a protein to be hydrolytically cleaved from the terminus, resulting in an increase in the amount of free amino acids and an improvement in umami taste of the food products. The free amino acid to be increased is not limited, but examples thereof include a hydrophobic amino acid such as leucine, isoleucine and phenylalanine, or tyrosine and methionine.

The use of the enzyme composition for food products enables such a food product as a custard cream to be improved in viscosity, leading to an improvement in texture such as smoothness. This is presumed to be due to the tendency of the enzyme composition for food products to remove hydrophobic amino acids by hydrolytic cleavage, thereby shifting the overall protein to hydrophilic.

The enzyme composition for food products has substantially no contaminating activity and can therefore reduce the bitter taste, harsh taste, astringent taste and odd taste in food products caused by the contaminating activity. A cow milk, a camel milk, a donkey milk, a goat milk, a horse milk, a sheep milk, a soybean, a pea, brown rice and the like have a peculiar odor which may adversely affect the palatability. The treatment with conventional enzyme compositions emphasizes the odor due to their contaminating activity resulting in further reduction in the palatability, whereas the use of the enzyme composition for food products of the present invention can reduce the odor, resulting in an improvement in the palatability.

EXAMPLES

Hereinafter, the present invention will be described in more detail with reference to Examples, but the present invention is not limited thereto. The unit "part (s)" or "%" means "part (s) by weight" or "% by weight", respectively, unless otherwise specified.

The following enzymes were used in the tests described below. The blending amount (%) described below is a value by weight for each substance.

Streptomyces-derived aminopeptidase

Aspergillus oryzae (koji mold)-derived peptidase (Product name: Flavourzyme 1000L; Novozymes Japan Ltd.)

Aspergillus oryzae (koji mold)-derived protease (product name: Denazyme AP; Nagase ChemteX Corporation)

Commercially available protease preparation 1

(1) Measurement Test of Enzyme Activity (Example 1 and Comparative Examples 1 and 2)

The protease activity, amylase activity and aminopeptidase activity were measured for Streptomyces-derived aminopeptidase (Example 1), Aspergillus oryzae (koji mold)-derived peptidase (Comparative Example 1) and Aspergillus oryzae (koji mold)-derived peptidase (Comparative Example 2), respectively.

For measurement of the protease activity, the amount of the enzyme that causes an increase in the colored substance in a Folin's test solution equivalent to 1 μg of L-tyrosine per minute as measured using milk casein as a substrate at 30° C. and pH 7.5 for 10 minutes is defined as 1 U.

For measurement of the amylase activity, the enzyme activity that reduces, the absorbance at a wavelength of 660 nm as measured using potato starch as a substrate at 40° C. and pH 6.0 for 10 minutes, by 1% per minute relative to the absorbance as measured using purified water as a control is defined as 1 U.

For measurement of the activity of the aminopeptidase, the amount of the enzyme that generates 1 μmol of paranitroaniline per minute as measured using L-leucyl-p-nitroanilide hydrochloride as a substrate at 37° ° C. and pH 8.0 for 10 minutes is defined as 1 U. In addition, the amylase activity per 1 U of aminopeptidase activity (A/P) and the protease activity per 1 U of aminopeptidase activity (E/P) were calculated.

Table 1 shows the results. Streptomyces-derived aminopeptidase (Example 1) has significantly lower protease activity and amylase activity, which are contaminating activities, and has lower A/P and E/P values, compared to Aspergillus oryzae (koji mold)-derived protease (Comparative Example 1) and Aspergillus oryzae (koji mold)-derived peptidase (Comparative Example 2). Some of the Streptomyces-derived aminopeptidases used in Examples 2 to 11 were different in lot from that in Example 1 and were thereby slightly different in activity, but the activity ratios A/P and E/P satisfied A/P<0.1 and E/P<0.3.

(2) Production Test of Beef Extract (Example 2 and Comparative Examples 3 to 5)

A 40 g portion of tap water was added to 20 g of minced beef to disperse it in the tap water followed by adding each enzyme thereto. The minced beef dispersion having the enzyme added was allowed to react at 50° C. to 55° C. for 3 hours without adjusting the pH. Thereafter, the enzyme was subjected to inactivation treatment in boiling water for 20 minutes, and the solids were filtered out through a filter paper to obtain a beef extract.

The protein concentration of the beef extract treated with the enzyme was measured with a DC protein assay kit (Bio-Rad Laboratories, Inc.). The tastes of the beef extract treated with the enzyme was evaluated by a sensory test. The free amino acids in the beef extract treated with the enzyme were analyzed by a PTC (phenylthiocarbamoyl) method.

Table 2 shows the test results of the Production test of beef extract for a beef extract produced with no enzyme (Comparative Example 3); a beef extract produced only with 0.1% of a commercially available protease preparation 1 relative to minced beef (Comparative Example 4); a beef extract produced with 0.1% of a commercially available protease preparation 1 and 1.0% of Aspergillus oryzae (koji mold)-derived peptidase relative to minced beef (Comparative Example 5); and a beef extract produced with 0.1% of a commercially available protease preparation 1 and 0.35% of Streptomyces-derived aminopeptidase relative to minced beef (Example 2). For Example 2 in which the beef extract was produced with Streptomyces-derived aminopeptidase, the bitter taste and harsh taste caused by the commercially available protease preparation 1 in Comparative Example 4 were absent, and the umami taste was improved.

The taste of each beef extract was evaluated by three panelists. The evaluation was performed, after oral ingestion of a certain amount of each extract, by rating it on a score of 1 to 5 for each of the bitter taste and umami taste according to the following criteria. At the time of evaluation, after confirming that the tastes had disappeared from the oral cavity, the next sample was evaluated.

Scores for bitter taste or umami taste:

5: felt very strongly;

4: felt strongly;

3: felt;

2: little felt; and

1: not felt.

Table 2 shows the results of determining the average value of the scores of the umami taste rated by the three panelists, according to the following criteria:

4 or more: excellent;

3 or more and less than 4: good;

2 or more and less than 3: average; and less than 2: poor.

Table 2 shows the results of determining the average value of the scores of the bitter taste rated by the three panelists, according to the following criteria:

TABLE 1

| | Protease activity (E) | Amylase activity (A) | Aminopeptidase activity (P) | A/P | E/P |
|---|---|---|---|---|---|
| (Example 1) Streptomyces-derived aminopeptidase | 13 | 0.5 | 1000 | 0.0005 | 0.01 |
| (Comparative Example 1) Aspergillus oryzae (koji mold)-derived protease | 60840 | 27100 | 770 | 35.2 | 79.0 |
| (Comparative Example 2) Aspergillus oryzae (koji mold)-derived peptidase | 24680 | 12000 | 1500 | 8.0 | 16.5 |

4 or more: poor;
3 or more and less than 4: average;
2 or more and less than 3: good; and
less than 2: excellent.

TABLE 2

| | Protein | Sensory test | | |
| --- | --- | --- | --- | --- |
| | concentration | Bitter taste | Umami taste | Results of taste test |
| Comparative Example 3 | 4.5 | Average | Good | Neither bitter taste nor umami taste |
| Comparative Example 4 | 44.0 | Poor | Good | Little umami taste; Strong bitter taste and some harsh taste |
| Comparative Example 5 | 45.2 | Poor | Excellent | Umami taste improved over that in Comparative Example 4, but some bitter taste left |
| Example 2 | 39.9 | Average | Excellent | Harsh taste as in Comparative Example 4 eliminated, and umami taste improved |

For Comparative Examples 3 and 4, umami taste was insufficient, and for Comparative Example 5, umami taste was strong but bitter taste was also strong. For Example 2, umami taste was able to be emphasized while suppressing bitter taste.

The analysis results of the free amino acids are shown in FIG. 1. After treatment with *Streptomyces*-derived aminopeptidase (Example 2), a large amount of hydrophobic amino acids such as leucine, isoleucine and phenylalanine were liberated. For Example 2, even though the amount of enzyme used was less than that for Comparative Example 5, amino acids equal to or more than those for Comparative Example 5 had been liberated.

panelists. The evaluation was performed, after oral ingestion of a certain amount of each modified egg yolk, by rating it on a score of 1 to 5 according to the following criteria. At the time of evaluation, after confirming that the taste had disappeared from the oral cavity, the next sample was evaluated.

Scores for sweet taste:
5: felt very strongly;
4: felt strongly;
3: felt;
2: little felt; and
1: not felt.

Table 3 shows the average value of the scores of the sweet taste rated by the three panelists. As shown in Table 3, excessive sweet taste was able to be reduced for Example 3, compared to that for Comparative Examples 6 to 8.

TABLE 3

| | | Enzymatic treatment at 50° C. | | Enzymatic treatment at 60° C. | |
| --- | --- | --- | --- | --- | --- |
| | Enzyme used | Sensory test | Results of taste test | Sensory test | Results of taste test |
| Comparative Example 6 | No enzyme | 3 | Sweet | 3 | Sweet |
| Comparative Example 7 | *Aspergillus oryzae* (koji mold)-derived protease | 2.6 | Liqueur flavor A little bit of bitter taste | 2.6 | A little bit of liqueur flavor harsh taste |
| Comparative Example 8 | *Aspergillus oryzae* (koji mold)-derived peptidase | 2.8 | Flavor like soy sauce Umami taste | 2.8 | Flavor like soy sauce Umami taste |
| Example 3 | Streptomyces-derived aminopeptidase | 2.5 | Flavor Mild sweet taste | 2.5 | Flavor Mild sweet taste |

(3) Egg Yolk Modification Test (Example 3 and Comparative Examples 6 to 8)

Each of the enzymes listed in Table 3 was dispersed in 50 mL of tap water in the amount corresponding to 0.5% relative to that of egg yolk. This enzyme liquid was added to 300 g of 20% sugar-added egg yolk (Kewpie Corporation) and allowed to react in a water bath at 50° C. or 60° C. for 1 hour. After completion of the reaction, the mixture was allowed to cool to room temperature.

The results of the taste test for each modified egg yolk are shown in Table 3 (Results of taste test). For Example 3, the flavor was able to be improved over that for Comparative Examples 6 and 7 and a different flavor from that for Comparative Example 8 was able to be obtained. The sweet taste of each modified egg yolk was evaluated by three (4) Production Test of Custard Cream (Example 4 and Comparative Examples 9 to 11)

A 600 g portion of milk (product name: Sogen Sanka (Long Life); Marubishi Co., Ltd.) and butter (Yotsuba Milk Products Co., Ltd.) were placed in a pan, and allowed to boil. The egg mixture obtained in (3) egg yolk modification test was placed in another pan; 100 g of sifted wheat flour (product name: SIRIUS; NIPPN CORPORATION) was added thereto; and the boiled milk and butter were added in small portions thereto while keeping mixing. After mixing, the mixture was heated over medium heat while keeping mixing until it became glossy and thickened into a paste to obtain a dough. The dough was wrapped in plastic wrap and stored in a refrigerator overnight. The next day was defined as day 0, and the viscosity was measured on day 1, day 3 and day 6. The sensory evaluation was performed only on day 0.

The viscosity was measured with a digital viscometer VISCO (ATAGO CO., LTD.). Specifically, a certain amount of a custard cream that had been conditioned to ordinary temperature before measurement was placed in a dedicated beaker and the viscosity was measured with a spindle A3.

Table 4 shows the results of the taste test for the custard cream. For Example 4, a mild sweetness and a smoother and softer texture were achieved. For Comparative Example 9, a pasty custard cream was able to be obtained, but the texture was poor. For Example 4, a pasty custard cream was obtained after about 10 minutes of mixing, but for Comparative Examples 10 and 11, no pasty custard cream was obtained even after 30 minutes of mixing. This is presumed to be due to the activity of contaminating amylase contained in the enzyme.

The texture of each custard cream was evaluated by three panelists. The evaluation was performed, after oral ingestion of a certain amount of each custard cream, by rating it on a score of 1 to 5 for smoothness according to the following criteria.

Scores of smoothness
5: Very smooth
4: High in smoothness
3: Smoothness felt
2: Low in smoothness
1: Not smooth Table 4 shows the results of determining the average value of the scores of the smoothness rated by the three panelists, according to the following criteria:

4 or more: excellent;
3 or more and less than 4: good;
2 or more and less than 3: average; and
less than 2: poor.

aminopeptidase and commercially available protease preparation 1 was added thereto in the amount shown in Table 5, and the mixture was subjected to an enzymatic reaction at 50° C. for 2 hours under the condition of unadjusted pH. After inactivating the enzyme by heating, the mixture was filtered through a No. 2 filter paper, and the residue on the filter was dried in vacuum.

The smell of each of the obtained extracts was evaluated by five panelists. The evaluation was performed, after oral ingestion of a certain amount of each extract, by rating it on a score of 0 to 3 for each of the bitter taste and umami taste according to the following criteria. At the time of evaluation, after confirming that the tastes had disappeared from the oral cavity, the next sample was evaluated.

0: Not felt
1: Felt faintly
2: Felt
3: Felt strongly

Table 5 shows the results of determining the average value of the scores of the umami taste rated by the five panelists, according to the following criteria:

2 or more: good;
1 or more and less than 2: average;
less than 1: poor.

Table 5 shows the results of determining the average value of the scores of the bitter taste rated by the five panelists, according to the following criteria:

2 or more: poor;
1 or more and less than 2: average; and
less than 1: good.

TABLE 4

| Custard cream | Modified egg yolk | Enzymatic treatment at 50° C. | | Enzymatic treatment at 60° C. | |
|---|---|---|---|---|---|
| | | Sensory test for smoothness | Results of taste test | Sensory test for smoothness | Results of taste test |
| Comparative Example 9 | Comparative Example 6 | Good | Sweet, powderful | Good | Less sweet than that treated at 50° C.; hard |
| Comparative Example 10 | Comparative Example 7 | Poor | Not pasty; strong in initial taste | Poor | Not pasty; strong in initial taste |
| Comparative Example 11 | Comparative Example 8 | Poor | Not pasty; mild in soy sauce feeling | Poor | Not pasty; soy sauce feeling disappeared; sweet |
| Example 4 | Example 3 | Excellent | Mild in sweetness; Smooth and soft | Excellent | Milder in sweetness, smoother and softer than that treated at 50° C. |

For Comparative Example 9, the smoothness was moderate, and for Comparative Examples 10 and 11, no paste was obtained. For Example 4, the smoothness was able to be improved.

Figure 2:
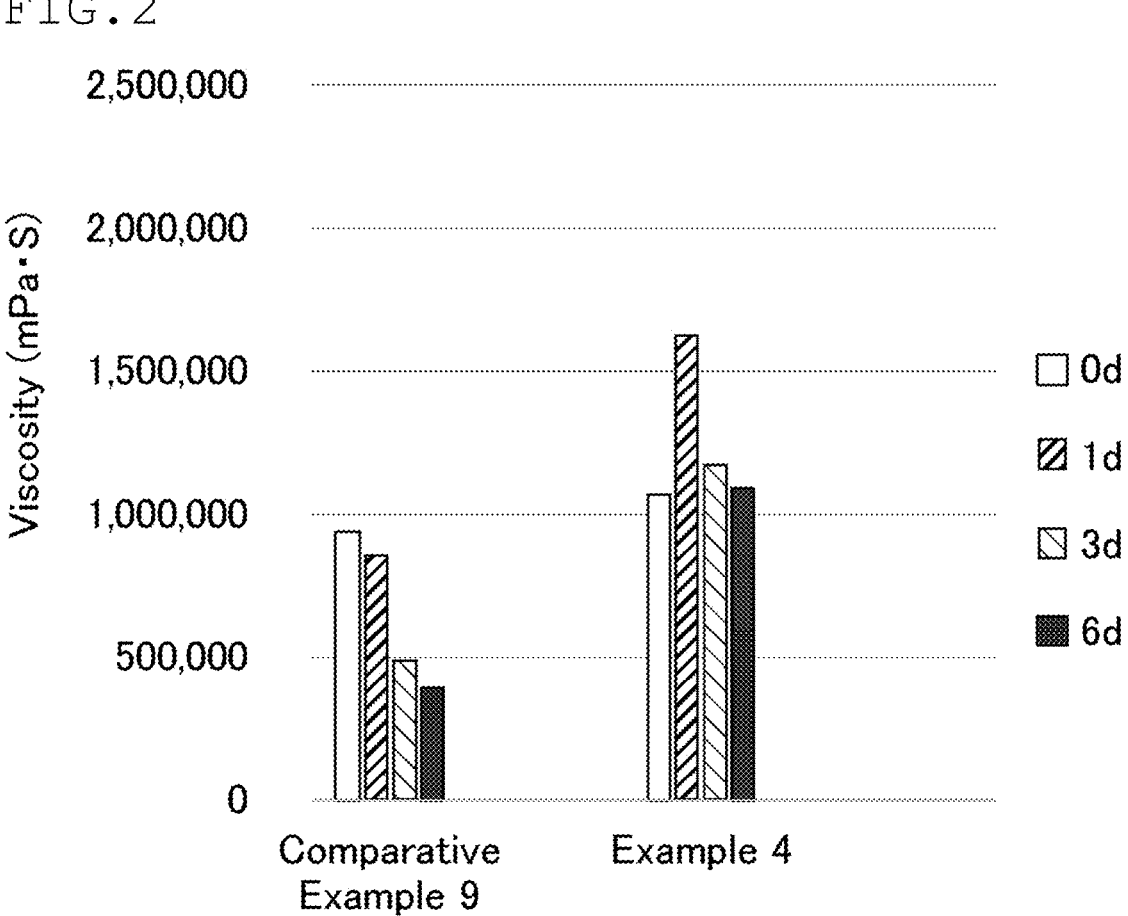
FIG. 2 shows the viscosity of the custard cream produced using the egg yolk subjected to enzymatic treatment.

FIG. 2 shows the viscosity of the custard cream produced using the egg yolk subjected to enzymatic treatment at 50° C. For Example 4, the custard cream showed higher viscosity than that for Comparative Example 9 in any storage period.

(5) Production Test of Seafood Extract 1 (Example 5 and Comparative Example 12)

Dried squid was finely cut and crushed with a food mill before use. The crushed dried squid of 10 g was swollen by adding 30 g of water thereto, and then sterilized at 100° C. for 60 minutes. Thereafter, each of *Streptomyces*-derived

TABLE 5

| | Example 5 | Comparative Example 12 |
|---|---|---|
| Streptomyces-derived aminopeptidase | 0.06 g | — |
| Commercially available protease preparation | 0.06 g | 0.06 g |
| Protease activity (U) | 49800.1 | 49800 |
| Aminopeptidase activity (U) | 60 | 0 |
| Umami taste | Good | Poor |
| Bitter taste | Good | Average |

As compared to Comparative Example 12, for Example 5, bitter taste was able to be reduced and umami taste was able to be enhanced.

(6) Enzymatic Treatment Test for Milk (Example 6 and Comparative Examples 13 to 16)

Each of the enzymes shown in Table 6 was added to 50 g of a commercially available whole milk, and the mixture was subjected to an enzymatic reaction at 52° C. for 3 hours. Table 6 shows the weight of the enzyme added as well as the protease activity and aminopeptidase activity equivalent to the weight. After completion of the enzymatic reaction, the enzyme was inactivated by treatment at 100° C. for 10 minutes.

For the activity of the aminopeptidase, the enzyme activity that generates 1 μmol of paranitroaniline per minute as measured using L-leucyl-p-nitroanilide hydrochloride as a substrate at 37° C. and pH 8.0 for 10 minutes is defined as 1 U. For the protease activity, the amount of the enzyme that causes an increase in the colored substance in a Folin's test solution equivalent to 1 μg of L-tyrosine per minute as measured using milk casein as a substrate at 30° C. and pH 7.5 for 10 minutes is defined as 1 U.

The smell and taste of each milk after the enzymatic treatment was evaluated by three panelists. The evaluation was performed, after oral ingestion of a certain amount of each milk subjected to enzymatic treatment, by rating it on a score of 1 to 5 for each of the smell and taste according to the following criteria. At the time of evaluation, after confirming that the taste had disappeared from the oral cavity, the next sample was evaluated.

5: Strong in odd taste and other smell than milk

4: Odd taste and other smell than milk

3: Odd taste and other smell than milk reduced but odor peculiar to milk

2: Neither odd taste nor other smell than milk, and low in odor peculiar to milk 1: Neither odd taste nor other smell than milk, and no odor peculiar to milk Table 6 shows the results of determining the average value of the scores of each of the smell and taste rated by the three panelists, according to the following criteria:

4 or more: poor;

3 or more and less than 4: average;

2 or more and less than 3: good; and less than 2: excellent.

For each of Comparative Examples 13 to 16, an odor peculiar to milk was felt, and odd taste and other smell than milk were left. In contrast, for Example 6, odd taste and other smell than milk were able to be eliminated and an odor peculiar to milk was able to be reduced.

(7) Enzymatic Treatment Test for Defatted Soybean (Example 7 and Comparative Examples 17 to 19)

A 35 g portion of defatted soybean (FUJIPRO FM ###, FUJI OIL CO., LTD.) was mixed with and dispersed in 700 g of water to provide a dispersion. Each of the enzyme in the amount shown in Table 7 was added to 100 mL of each dispersion dispensed, and the mixture was then subjected to an enzymatic reaction at 52° C. for 3 hours. After completion of the enzymatic reaction, the enzyme was inactivated by treatment at 100° C. for 10 minutes.

The taste of each defatted soybean after the enzymatic treatment was evaluated by three panelists. The evaluation was performed, after oral ingestion of a certain amount of each defatted soybean subjected to enzymatic treatment, by rating it on a score of 1 to 5 for each of the strengths of bitter taste and soybean flavor according to the following criteria. At the time of evaluation, after confirming that the taste had disappeared from the oral cavity, the next sample was evaluated.

5: Felt very strongly;

4: Felt strongly;

3: Felt;

2: Little felt; and

1: Not felt.

Table 7 shows the results of determining the average value of the scores of each of the strengths of bitter taste and soybean flavor rated by the three panelists, according to the following criteria:

4 or more: poor;

3 or more and less than 4: average;

2 or more and less than 3: good; and less than 2: excellent.

TABLE 6

| | | Example | Comparative Example | | | |
|---|---|---|---|---|---|---|
| | | 6 | 13 | 14 | 15 | 16 |
| Enzyme | Enzyme name | Streptomyces-derived aminopeptidase | (No enzyme added) | *Aspergillus oryzae* (koji mold)-derived protease | *Aspergillus oryzae* (koji mold)-derived peptidase | Commercially available protease preparation 1 |
| | Amount added g | 0.1 | — | 0.15 | 0.075 | 0.05 |
| | Protease activity (U) | 1 | — | 9000 | 1800 | 41500 |
| | Aminopeptidase activity (U) | 90 | — | 90 | 90 | 0 |
| Sensory test | Smell | Good | Average | Poor | Average | Average |
| | Taste | Excellent | Average | Poor | Poor | Poor |

TABLE 7

| | | Example | Comparative Example | | |
|---|---|---|---|---|---|
| | | 7 | 17 | 18 | 19 |
| Enzyme | Enzyme name | Streptomyces-derived aminopeptidase | (No enzyme added) | Commercially available protease preparation 1 | *Aspergillus oryzae* (koji mold)-derived protease |
| | Amount added (g) | 0.05 | — | 0.01 | 0.01 |
| | Protease activity (U) | 0.5 | — | 8300 | 600 |
| | Aminopeptidase activity (U) | 45 | — | 0 | 6 |
| Sensory test | Soybean flavor | Excellent | Average | Good | Good |
| | Bitter taste | Excellent | Average | Poor | Poor |

For Comparative Examples 17 to 19, bitter taste was left, and soybean taste was also left. For Example 7, both bitter taste and soybean taste can be eliminated to obtain a treated soybean product to be easily ingested as a protein source.

(8) Enzymatic Treatment Test for Plain Soymilk (Example 8 and Comparative Examples 20 to 22)

Each of the enzymes shown in Table 8 was added to 50 g of a commercially available plain soymilk, and the mixture was then subjected to an enzymatic reaction at 52° C. for 3 hours. After completion of the enzymatic reaction, the enzyme was inactivated by treatment at 100° C. for 10 minutes.

The taste and smell of each plain soymilk after the enzymatic treatment was evaluated by three panelists. The evaluation was performed, after oral ingestion of a certain amount of each plain soymilk subjected to enzymatic treatment, by rating it on a score of 1 to 5 for each of the taste (the strength of bitter taste and odd taste) and smell (the strength of unpleasant odor) according to the following criteria. At the time of evaluation, after confirming that the tastes had disappeared from the oral cavity, the next sample was evaluated.

5: Felt very strongly;
4: Felt strongly;
3: Felt;
2: Little felt; and
1: Not felt.

Table 8 shows the results of determining the average value of the scores of each of the taste and smell rated by the three panelists, according to the following criteria:

4 or more: poor;
3 or more and less than 4: average;
2 or more and less than 3: good; and
less than 2: excellent.

For Comparative Examples 20 to 22, bitter taste, odd taste and unpleasant odor were left. For Example 8, bitter taste, odd taste and unpleasant odor were able to be reduced to obtain a soymilk to be easily ingested as a protein source.

(9) Enzymatic Treatment Test for Insect-Derived Protein (Example 9 and Comparative Examples 23 and 24)

5 g of cricket powder obtained by grinding was added to 50 g of water, and the enzymes shown in Table 9 were added to the mixture, and then the resultant was subjected to enzymatic reaction at 52° C. for 3 hours. After completion of the enzymatic reaction, the enzymes were inactivated by treatment at 100° C. for 10 minutes. The reaction solution was filtrated through a filter paper to collect the liquid fraction as the extract.

The taste of each extract was evaluated by seven panelists. The evaluation was performed, after oral ingestion of a certain amount of each extract, by rating it on a score of 1 to 5 for each of the strengths of bitter taste and astringent taste according to the following criteria. At the time of evaluation, after confirming that the tastes had disappeared from the oral cavity, the next sample was evaluated.

5: Felt very strongly;
4: Felt strongly;
3: Felt;
2: Little felt; and
1: Not felt.

Table 9 shows the results of determining the average value of the scores of the strength of bitter taste and astringent taste rated by the seven panelists, according to the following criteria:

4 or more: poor;
3 or more and less than 4: average;
2 or more and less than 3: good; and
less than 2: excellent.

TABLE 8

| | | Example | Comparative Example | | |
|---|---|---|---|---|---|
| | | 8 | 20 | 21 | 22 |
| Enzyme | Enzyme name | Streptomyces-derived aminopeptidase | (No enzyme added) | *Aspergillus oryzae* (koji mold)-derived protease | *Aspergillus oryzae* (koji mold)-derived peptidase |
| | Amount added (g) | 0.1 | — | 0.15 | 0.075 |
| | Protease activity (U) | 1 | — | 9000 | 1800 |
| | Aminopeptidase activity (U) | 90 | — | 90 | 90 |
| Sensory test | Smell | Good | Average | Average | Good |
| | Taste | Excellent | Average | Poor | Average |

TABLE 9

| | Example | Comparative Example | |
|---|---|---|---|
| | 9 | 23 | 24 |
| Streptomyces-derived aminopeptidase | 0.05 g | — | — |
| *Aspergillus oryzae* (koji mold)-derived protease | 0.05 g | — | 0.1 g |
| Sensory test | Good | Good | Average |

For Comparative Example 24, both bitter taste and astringent taste were strong. For Example 9, both bitter taste and astringent taste were able to be reduced to obtain an insect extract to be easily ingested as a protein source.

(10) Enzymatic Treatment Test for Yeast Extract (Examples 10 and 11 and Comparative Examples 25 to 27)

A 15 g portion of dry yeast was mixed with 135 g of tap water to prepare a 10% by weight yeast solution, which was pre-incubated at 55° C. for 1.5 hours. Each enzyme was added in the amount that provides the protease activity or aminopeptidase activity listed in Table 10. In Example 11, the amounts to be added of the two enzymes, protease and aminopeptidase was adjusted so as to obtain the desired protease activity and aminopeptidase activity, respectively. Thereafter, the mixture was subjected to an enzymatic reaction at 55° C. for 3.5 hours under the condition of unadjusted pH. After completion of the enzymatic reaction, the enzyme was inactivated by treatment at 100° C. for 10 minutes. The reaction liquid was centrifuged for 10 minutes under the conditions at 20° C. and 9,000 rpm, and the supernatant was collected as an extract.

The taste of each extract was evaluated by four panelists. The evaluation was performed, after oral ingestion of a certain amount of each extract, by rating it on a score of 1 to 5 for each of the strengths of umami taste and bitter taste according to the following criteria. At the time of evaluation, after confirming that the tastes had disappeared from the oral cavity, the next sample was evaluated.

5: Felt very strongly;
4: Felt strongly;
3: Felt;
2: Little felt; and
1: Not felt.

Table 10 shows the results of determining the average value of the scores of the umami taste rated by the four panelists, according to the following criteria:

4 or more: excellent;
3 or more and less than 4: good;
2 or more and less than 3: average; and
less than 2: poor.

Table 10 shows the results of determining the average value of the scores of the bitter taste rated by the four panelists, according to the following criteria:

4 or more: poor;
3 or more and less than 4: average;
2 or more and less than 3: good; and
less than 2: excellent.

TABLE 10

| | | Example | | Comparative Example | | |
|---|---|---|---|---|---|---|
| | | 10 | 11 | 25 | 26 | 27 |
| Enzyme | Enzyme name | Streptomyces-derived aminopeptidase | Streptomyces-derived aminopeptidase and *Aspergillus oryzae* (koji mold)-derived protease | (No enzyme added) | Commercially available protease preparation 1 | *Aspergillus oryzae* (koji mold)-derived protease |
| | Protease activity (U) | 10 | 6000 | — | 124500 | 27000 |
| | Aminopeptidase activity (U) | 300 | 260 | — | 0 | 270 |
| Sensory test | Umami taste | Good | Excellent | Good | Poor | Poor |
| | Bitter taste | Good | Good | Average | Poor | Poor |

For Comparative Example 25, umami taste was felt but bitter taste was strong, and for Comparative Examples 26 and 27, umami taste was not felt and bitter taste was very strong. For Examples 10 and 11, umami taste was able to be improved while suppressing bitter taste.

The invention claimed is:

1. A method of producing a food product, comprising:

processing a food material with an enzyme composition comprising a peptidase and having substantially no contaminating activity, thereby hydrolytically cleaving a peptide bond of a polypeptide chain in the food material, wherein the food product has at least one property that is improved compared with the at least one property of a food product comprising a food material that is processed with an enzyme composition having the contaminating activity, the at least one property being selected from the group consisting of umami taste, texture, odd taste, odor, sweet taste, and astringent taste.

2. The method according to claim 1, wherein the food material is a meat, a seafood, an egg, a milk, a plant, an insect, or a microorganism culture.

3. The method according to claim 1, wherein the contaminating activity is an amylase activity or a protease activity.

4. The method according to claim 1, wherein the enzyme composition has an A/P ratio of 0.1 or less, where A represents an amylase activity and P represents a peptidase activity.

5. The method according to claim 1, wherein the enzyme composition has an E/P ratio of 0.3 or less, where E represents a protease activity and P represents a peptidase activity.

6. The method according to claim 1, wherein the peptidase is aminopeptidase.

7. The method according to claim 1, wherein the enzyme composition is configured to be used in a production of processed meat food products, processed seafood food products, processed egg food products, processed dairy food products, processed plant food products, insect food products, or seasonings.

* * * * *

SEQUENCE LISTING

```
<160> NUMBER OF SEQ ID NOS: 2

<210> SEQ ID NO 1
<211> LENGTH: 345
<212> TYPE: PRT
<213> ORGANISM: Streptomyces septatus TH-2

<400> SEQUENCE: 1

Met Leu Glu Leu Asn Gly Pro Leu Asn Gly Pro Ala Arg Arg Ser Arg
1               5                   10                  15

Ala Val Ala Leu Leu Ala Thr Gly Ala Ala Leu Ala Ala Thr Leu Leu
```

```
                20              25              30

Gly Thr Ala Ser Gly Ala Ala Asp Ala Val Pro Thr Thr Ala Lys Thr
            35              40              45

Thr Ala Thr Thr Ala Ala Ala Lys Gly His Val Arg Thr Lys Ala Gly
    50              55              60

Ala Pro Ala Ile Pro Val Ala Asn Val Lys Ala His Leu Asn Gln Leu
65              70              75              80

Gln Ser Ile Ala Arg Ala Asn Asn Gly Asn Arg Ala His Gly Arg Ser
            85              90              95

Gly Tyr Lys Ala Ser Val Asp Tyr Val Lys Gly Lys Leu Asp Ala Ala
            100             105             110

Gly Phe Thr Thr Thr Val Gln Gln Phe Ser Ala Asn Gly Ala Thr Gly
            115             120             125

Tyr Asn Leu Ile Ala Asp Trp Pro Gly Gly Asp Thr Asp His Val Val
            130             135             140

Phe Ala Gly Ser His Leu Asp Ser Val Ser Ala Gly Pro Gly Ile Asn
145             150             155             160

Asp Asn Gly Ser Gly Ser Ala Gly Val Leu Glu Val Ala Leu Ala Val
            165             170             175

Ala Arg Glu Gly Tyr Lys Pro Asp Lys His Leu Arg Phe Gly Trp Trp
            180             185             190

Gly Ala Glu Glu Leu Gly Met Val Gly Ser Gln Asn Tyr Val Asp Asn
            195             200             205

Leu Ser Ser Ala Asp Arg Ser Lys Ile Asp Ala Tyr Leu Asn Phe Asp
    210             215             220

Met Ile Gly Ser Pro Asn Pro Gly Tyr Tyr Val Tyr Gly Tyr Asp Ala
225             230             235             240

Asn Leu Gln Ser Leu Phe Glu Asn Trp Phe Ala Ala Lys Asn Ile Ala
            245             250             255

Thr Glu Val Asp His Glu Gly Asp Gly Arg Ser Asp His Ala Pro Phe
            260             265             270

Gln Asn Val Gly Ile Pro Val Gly Gly Leu Phe Ser Gly Ala Asp Tyr
            275             280             285

Ile Lys Thr Ala Glu Gln Ala Gln Lys Trp Gly Gly Thr Ala Gly Arg
    290             295             300

Ala Phe Asp Ala Cys Tyr His Arg Ser Cys Asp Thr Tyr Ala Asn Leu
305             310             315             320

Asn Asp Thr Ala Leu Gly Thr Asn Thr Asp Ala Ile Ala Gly Ala Val
            325             330             335

Trp Ser Leu Ser Gly Ser Ala Thr Ser
            340             345
```

<210> SEQ ID NO 2
<211> LENGTH: 1038
<212> TYPE: DNA
<213> ORGANISM: Streptomyces septatus TH-2

<400> SEQUENCE: 2
atgcttgaac tcaacggacc actcaacgga cctgcccgga gaagccgcgc cgtcgccctc      60
ctggccaccg gcgcggccct cgccgccacc ctcctcggca cggcctccgg cgcggccgac     120
gcggtcccca ccaccgcgaa gaccaccgcc accaccgccg ccgccaaggg ccacgtcagg     180
accaaggccg gcgcgcccgc catccccgtg gccaacgtca aggcccatct caaccagctc     240
cagtcgatag ccagggccaa caacggcaac cgcgcgcacg gccgcagcgg ttacaaggcg     300

-continued

```
tccgtcgact atgtgaaggg caagctggac gccgccggat tcaccaccac cgtgcagcag    360
ttcagcgcca acggcgccac cggctacaac ctgatagccg actggcccgg cggtgacacc    420
gaccacgtcg tcttcgccgg ctcgcacctc gactccgtct ccgcgggccc cggcatcaac    480
gacaacggct ccggctccgc cggtgtcctc gaagtcgccc tcgccgtcgc ccgcgagggc    540
tacaagcccg acaagcacct gcggttcggc tggtggggcg ccgaggaact cggcatggtc    600
ggctcgcaga actacgtcga caacctgtcc tccgccgacc ggtcgaagat cgacgcctat    660
ctgaacttcg acatgatcgg ctcgccgaac ccgggctact acgtctacgg ctacgacgcg    720
aacctccaga gcctcttcga gaactggttc gcggcgaaga acatcgccac cgaggtcgac    780
cacgagggcg acggccgctc ggaccacgcg cctttccaga acgtcggcat acccgtcggc    840
gggctcttca gcgcgccga ctacatcaag accgccgagc aggcgcagaa gtggggcggc    900
acggcgggcc gggcgttcga cgcctgctac caccgctcgt gcgacacgta cgccaacctg    960
aacgacaccg cgctcggcac gaacaccgat gcgatcgcgg gtgcggtgtg gtcgctgagc    1020
ggcagcgcca cgagctag                                                   1038
```